United States Patent
Van Bladel et al.

(10) Patent No.: US 7,049,346 B1
(45) Date of Patent: *May 23, 2006

(54) SWOLLEN HYDROGEL FOR SPHINCTER AUGMENTATION

(75) Inventors: Kevin H. Van Bladel, San Mateo, CA (US); Robert S. Bley, Menlo Park, CA (US); John D. Wallace, Fremont, CA (US)

(73) Assignee: Menlo Care Div of Ethicon, Inc., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/700,168

(22) Filed: Aug. 20, 1996

(51) Int. Cl.
*A61F 13/00* (2006.01)

(52) U.S. Cl. .................. 514/944; 523/113; 424/422; 424/423; 424/426; 424/430; 424/433

(58) Field of Classification Search ............... 424/486, 424/487, 488, 499, 501; 514/944, 952
See application file for complete search history.

(56) References Cited

U.S. PATENT DOCUMENTS

| | | | |
|---|---|---|---|
| 3,419,006 A | 12/1968 | King | 128/268 |
| 3,971,376 A | 7/1976 | Wichterle | 128/260 |
| 4,134,871 A | 1/1979 | Otani et al. | 260/29.6 |
| 4,197,846 A | 4/1980 | Bucalo | 128/218 |
| 4,272,518 A | 6/1981 | Moro et al. | 424/81 |
| 4,343,789 A * | 8/1982 | Kawata et al. | |
| 4,404,183 A * | 9/1983 | Kawata et al. | |
| 4,423,099 A * | 12/1983 | Mueller et al. | |
| 4,527,293 A | 7/1985 | Eckstein et al. | 623/12 |
| 4,698,373 A * | 10/1987 | Tateosian et al. | |
| 4,773,393 A | 9/1988 | Haber et al. | 600/30 |
| 4,777,200 A | 10/1988 | Dymond et al. | 524/458 |
| 4,803,075 A | 2/1989 | Wallace et al. | 424/423 |
| 4,828,828 A | 5/1989 | Trager et al. | 424/81 |
| RE32,969 E | 6/1989 | Trager et al. | 424/81 |
| 5,007,940 A | 4/1991 | Berg | 623/66 |
| 5,067,965 A | 11/1991 | Ersek et al. | 623/66 |
| 5,162,430 A | 11/1992 | Rhee et al. | 525/54.1 |
| 5,330,768 A * | 7/1994 | Park et al. | |
| 5,336,263 A | 8/1994 | Ersek et al. | 623/11 |
| 5,514,754 A * | 5/1996 | Henderson et al. | |

FOREIGN PATENT DOCUMENTS

EP        A 251 695        6/1987

(Continued)

OTHER PUBLICATIONS

Robert A. Ersek, M.D., F.A.C.S. and Arthur A. Beisang, III, M.D. Bioplastique: A New Biphasic Polymer for Minimally Invasive Injection Implantation Aesthetic Plastic Surgery 16:59-65, 1992.

(Continued)

*Primary Examiner*—Dwayne Jones
*Assistant Examiner*—Shirley V. Gembeh

(57) ABSTRACT

A physiologically acceptable composition comprises a plurality of physiologically acceptable hydrogel particles which have been swollen in a water solution containing a low molecular weight water soluble organic compound, the solution having the ability to swell the particles. The concentration of the organic compound is such that the resulting particles can be inserted, without use of a carrier liquid utilizing a hand driven hypodermic syringe. The swollen hydrogel particles are substantially insoluble in body fluids. The composition is useful for treating urinary tract disorders.

11 Claims, 2 Drawing Sheets

FOREIGN PATENT DOCUMENTS

| | | |
|---|---|---|
| EP | 0684045 A | 11/1995 |
| WO | WO A 86 01813 | 3/1986 |
| WO | WO A 93 16658 | 9/1993 |
| WO | WO A 93 19702 | 10/1993 |

OTHER PUBLICATIONS

European Search Report for EP 97/306281 dated Dec. 7, 1999.

* cited by examiner

SWOLLEN HYDROGEL FOR SPHINCTER AUGMENTATION

TECHNICAL FIELD

The invention relates to a composition comprising a plurality of swollen hydrogel particles which can be inserted in a patient's tissue without the need for a carrier liquid and to a method of forming such a composition. The invention further relates to a method of deforming a selected tissue structure by inserting into tissues adjacent to the selected tissue structure such a composition. Principally, the invention provides a treatment for those with urinary incontinence and/or vesicoureteral reflux.

BACKGROUND OF THE INVENTION

Surgical implantation of artificial sphincters has often been employed to treat patients suffering from urinary incontinence. The surgical implantation of the artificial sphincter commonly requires hospitalization. In addition, such a procedure is relatively complex and expensive, and will usually require six to eight weeks of recovery time. Moreover, often time, the procedure is unsuccessful or the artificial sphincter malfunctions. As a result, additional surgery is required to adjust, repair or replace the implant.

In the recent past, urinary incontinence may be successfully treated by using nonsurgical means.

A common and widely used method to treat patients with urinary incontinence is periurethral injection of a composition commercially sold in Canada as "Polytef" and as "Urethrin". "Polytef" is a paste comprising a fifty—fifty (50/50) by weight mixture of glycerine liquid and Teflon particles. However, after injection, over a period of time the glycerine is readily dissipated into the body and then metabolized or eliminated, leaving only the Teflon particles. This means that only fifty (50) percent of the injected weight remains at the injection site. Consequently the surgeon must inject significantly more volume than he thinks he will need and at times must actually close down the urethra further than is desired. This closure could possibly be complete and thus put the patient into temporary urinary retention. Additionally, the fact that a large portion of the volume disappears makes it difficult for the surgeon to visually gauge how much is an appropriate amount of the Teflon paste to inject. As a result, the surgeon is likely to not inject enough paste volume. The procedure therefore may fail, and a second or even a third procedure to inject additional paste may be required. An additional drawback of the Teflon paste is that the Teflon particle size is sufficiently small so as to allow the particles to migrate to other locations of the body such as the lungs, brain, etc. Teflon particles have been known to induce tissue reaction and form Teflon-induced granulomas in certain individuals. This tissue reaction to Teflon has caused concerns for the patient's safety. Also, the Teflon paste is highly viscous and can only be used by applying a large injection force (IF) injected using a hypodermic held by an injection assist device since the surgeon would not have sufficient strength to force the highly viscous Teflon paste through a needle of any acceptable size.

An alternative to using the Teflon paste is using a collagen suspension. The collagen suspension is injected in the same manner as Teflon paste so as to form a fibrous mass of tissue around the augmentation site. This fibrous mass created by the collagen injection, however, decreases in size and breaks down over time as it is eventually degraded by the patient's body. As a result, additional injections are periodically required.

Another alternative is to inject silicone particles dispersed in an aqueous, polyvinylpyrrolidone solution. This combination has the same problems as the Teflon paste in that the polyvinylpyrrolidone solution is readily dissipated away from the area of injection leaving only the volume of silicone particles remaining and in that due to its high viscosity a great deal of force is necessary to inject the silicone dispersion through a needle of an acceptable size whereby it is necessary for the surgeon to utilize an injection assist device to accomplish injection.

Another material that has been injected is autologous fat. This has had similar problems as the collagen in that the body eventually breaks it down and it disappears.

Devices have been made to attempt to overcome these problems. One device is an inflatable silicone sphere that is passed through a needle and is inflated with saline in the same area that the other materials are injected. There are, however, some problems associated with this device. It is a delicate, mechanical device that is capable of mechanical failure of the valves, shells and structural joints.

Accordingly, it would be desirable to have a composition which has sufficiently low injection force so that it is not necessary to utilize an injection assist device to inject it whereby it is easily administered via injection, generally will not change in volume following insertion, will be soft enough so as to not cause tissue response/reaction while still being firm enough to provide the required constriction, will not dissipate and will not migrate from the site of injection, thereby enabling the urethra to maintain the initial surgical constriction.

Berg, et al., in U.S. Pat. No. 5,007,940 have made an attempt to overcome the above set forth problems by utilizing fully hydrated hydrogel particles in disk form which deform as they pass through a needle during injection. The cost to synthesize such particles has, however, been so high that they have not been utilized commercially. Also, the particles have still exhibited a significantly high viscosity whereby their use has required the use of relatively large internal diameter needles and the use of relatively large injection forces to accomplish insertion in a patient. Thus, they have not served to fully overcome the problems of the prior art.

DISCLOSURE OF THE INVENTION

The present invention is directed to overcoming one or more of the problems as set forth above.

Applicant has surprisingly found that if hydrogel particles are swollen an aqueous medium and if they contain a water soluble organic compound, the resulting swollen hydrogel particles have very significantly lowered IFs as compared to the same hydrated particles which do not contain the organic compound. Indeed, there appears to be a range of ratios of the organic compound to water which is more effective for providing the reduction in IFs. If the ratio is below or above such range, the effect is significantly reduced.

Accordingly, an embodiment of the invention is a physiologically acceptable composition comprising a plurality of physiologically acceptable hydrogel particles which have been swollen by contact with an aqueous medium and which contain a low molecular weight water soluble organic compound, the ratio of the organic compound to the aqueous medium being such that the resulting particles require an IF significantly lower than that required in the absence of the organic compound, preferably of lower by at least 30%, more preferably by at least 50% and still more preferably by at least 65%. The swollen hydrogel particles are substantially insoluble in body fluids.

Accordingly, the invention provides a non-surgical procedure using an easily administered low injection force composition for treating patients with urinary incontinence. In addition, the invention can reduce the need for reinjections associated with the use of Teflon, collagen, silicone, autologous fat or other similar materials when treating patients with urinary incontinence. By having physiologically acceptable swollen hydrogel particles that will not break down, will not migrate, will not lead to adverse tissue reaction and can be injected without use of an injection assist device which provides a mechanical advantage. Due to their low injection force even without a carrier liquid, a more permanent repair is given to the incontinent patient. Similarly, because of the composition's properties, it can be used to treat patients suffering from vesicoureteral reflux. It can also be used in cosmetic or plastic surgeries.

BRIEF DESCRIPTION OF THE DRAWINGS

The invention will be better understood by reference to the figures of the drawings wherein like numbers denote like parts throughout and wherein.

BEST MODE FOR CARRYING OUT THE INVENTION

The physiologically acceptable composition can be used in various medical situations. Typically, the physiologically acceptable composition can be injected into tissues adjacent to a selected tissue structure thereby deforming the selected tissue structure. Preferred uses for this particular application are: 1) to provide a treatment for those with urinary incontinence wherein the urethra cannot be properly constricted to prevent passage of urine from the bladder, and 2) to provide a treatment for those with vesicoureteral reflux wherein the ureter cannot properly constrict to prevent backflow of urine from the bladder up the ureter.

A few terms should be defined so as to clarify the explanations which follow. The term "hydrated" is used to denote absorption of water alone. The term "swollen" is used to indicate an association or absorption of water or of water and an organic compound useful in the practice of the invention. Thus, a "swollen" particle will have absorbed at least the, water and may have absorbed the organic compound, as well. The swollen particle, as the adjective specifies, will have a larger size after swelling than it had prior to swelling. With these definitions in mind it should be easier to follow the discussion.

Figure 1:
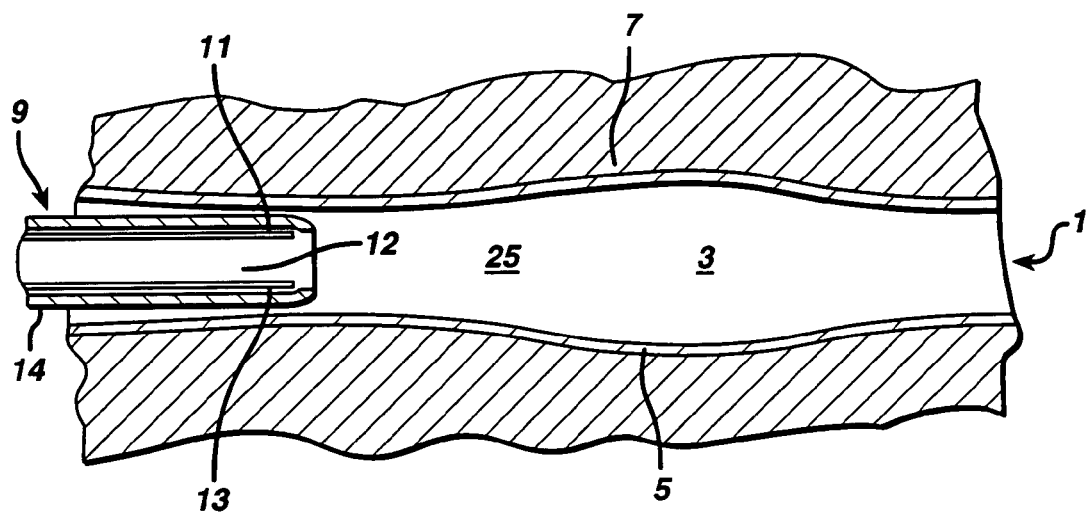
FIG. 1 is a longitudinal section of a tissue structure, more specifically a urethra/ureter, with an enlarged lumen surrounded by muscle tissues.

Referring to FIG. 1, there is shown a urethra/ureter 1 having a wall 5 and an enlarged lumen 3. The urethra/ureter 1 is surrounded by tissues 7. Before the enlarged lumen 3 is to be constricted with the physiologically acceptable composition, a cystoscope 9 comprising a fiberoptic light transmitting element 11, a working channel 12 and a viewing element 13 encased in a metallic sheath 14 is inserted up the urethra/ureter to a distance close to the enlarged lumen 3. The close distance is selected to allow a clear view of the enlarged lumen 3.

Figure 2:
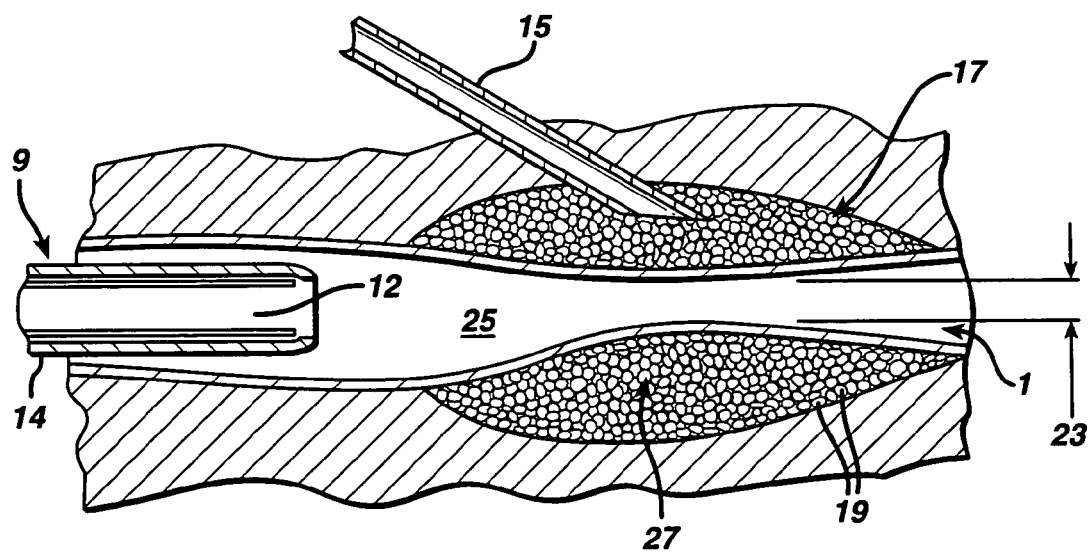
FIG. 2 shows the same longitudinal section immediately after a physiologically acceptable composition has been injected around the enlarged lumen of the urethra.

Once the enlarged lumen 3 is readily in view, referring more specifically to FIG. 2, a hypodermic needle 15 is inserted through the tissues 7, preferably over the enlarged lumen 3, stopping near the wall 5 of the enlarged lumen 3. Thereafter, a physiologically acceptable composition 17 is injected via the hypodermic needle 15 into the tissues 7 adjacent the wall 5.

Figure 3:
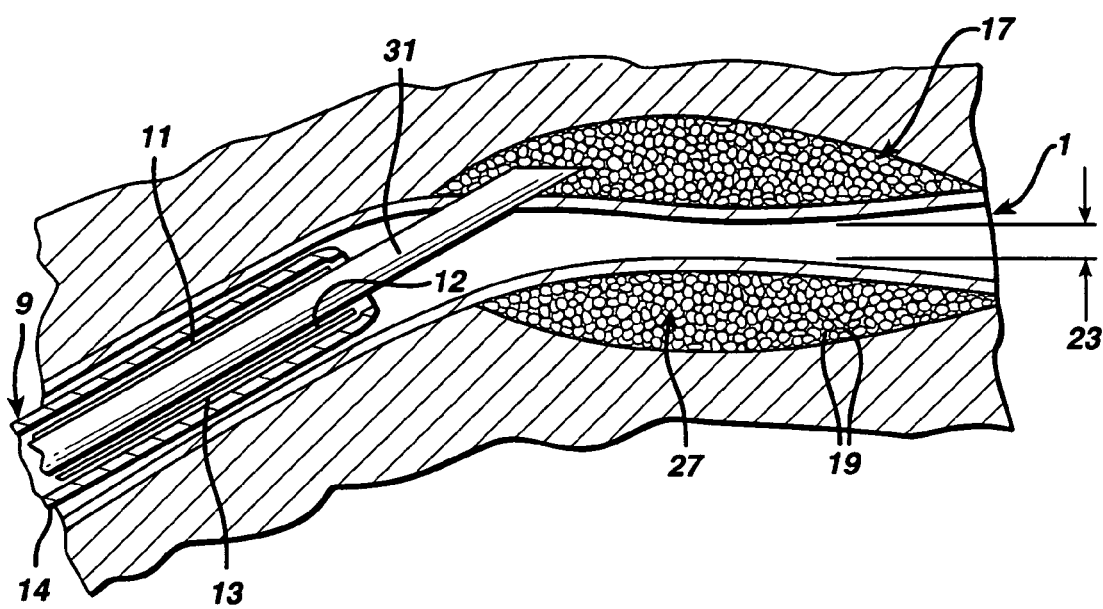
FIG. 3 shows the same longitudinal section as in FIG. 1 immediately after a physiologically acceptable composition has been injected around the enlarged lumen of the urethra/ureter utilizing a through the cystoscope injection technique.

As an alternative, and as is illustrated in FIG. 3, an elongated needle 31 may be inserted through the working channel 12, into the urethra/ureter 1 and the surrounding tissue and the injection can be completed operating solely through the cystoscope 9. This is generally the preferred method of operation on male patients urethra/ureter and is the preferred method for female patients for the ureter.

The physiologically acceptable composition 17 comprises a plurality of preswollen hydrogel particles 19. The particles may be used in a physiologically acceptable biodissipatable liquid carrier 21 but it is generally preferred to inject them with only a small amount of such a carrier liquid and, in such an instance, the carrier liquid is then normally only the interstitial water/organic compound mixture used to hydrate and swell the particles. Generally, the carrier liquid would then comprise no more that about 25%, more usually no more than about 15%, by volume of the overall composition. Such particles are generally solid which is not meant to preclude their containing one or more hollow spaces within their volumes.

The swollen hydrogel particles 19 suitable for the present invention must be physiologically acceptable and are preferably substantially insoluble in body fluids. When a liquid carrier is present the swollen hydrogel particles 19 must also be substantially insoluble in the liquid carrier.

The hydrogel particles 19 are small enough and have a low enough injection force, to be readily injectable via a needle. The particles preferably have a particle size sufficient to avoid migration. Migration to other parts of the body should be prevented because the particle may cause tissue reaction. One way of obtaining unswollen hydrogel particles 19 of the desired size is by cryogenic grinding of a larger piece or pieces of polymer prior to carrying out the swelling operation.

The hydrophilic component is suitably is a very highly cross-linked, hence a very high molecular weight (generally of molecular weight above about 400,000), poly(ethylene oxide) (PEO) polymer or copolymer, a polyvinylpyrrolidone (PVP) polymer or copolymer, a polyvinyl alcohol (PVA) polymer or copolymer, a pHema (poly(2-hydroxyethyl methacrylate) polymer or copolymer, a Hypan (hydrolyzed (polyacrylonitrile) polymer or copolymer, a dextran polymer or copolymer, a starch glycolate polymer or copolymer salt, a polyacrylic acid polymer or copolymer, or a polyacrylamide polymer or copolymer. The hydrophilic component absorbs at least about 35% water, preferably at least about 100% water, more preferably about 500% water or more, e.g., 2,000% water, by weight based on the weight of the hydrophilic polymer. The hydrophilic polymer forms a hydrogel on absorption of water. The hydrophilic polymer should not be degraded by body fluids within the site of injection for long periods of time, for example, one year, more preferably two years, still more preferably five years. Most preferably the hydrophilic polymer should be substantially completely nondegradable in that it should preferably be non-degradable for the life of the patient.

Preferably, the swollen hydrogel 19 is PEO (including copolymers thereof with, for example, polypropylene oxide, PPO). PEO having an initial (prior to irradiation and cross-linking) molecular weight of from 200,000 to 7,000,000 have been successfully tested in accordance with the invention and cross-linked using electron beam radiation and a cross-linking agent). The most preferred composition uses PEO having an initial molecular weight of about 400,000, a crosslinking agent as set forth above and applying from 5 to 20 Mrad of electron beam radiation.

Any organic compound which are water soluble and will swell the as yet not fully hydrated hydrogel with water/organic compound solution and will satisfy the other requirements mentioned above are useful in the practice of the present invention. Suitable organic compounds include, without limitation, polyethylene glycol, preferably of a molecular weight range from about 200 to about 1,000, PVP with a molecular weight below about 50,000, dextran with a molecular weight below about 1,000, polyoxyalkylene ether available from BASF Corporation under the tradename Pluronic having a molecular weight between about 400 and 1,000, polyacrylic acid having a molecular weight between about 400 and 1,000, polyacrylamide, polyvinyl pyridine, polylysine, polyarginine and oligo peptides such as polyaspartic acid and polyglutamic acid.

The relatively low injection force of the hydrogel particles allows injection using a relatively small needle on a hypodermic syringe which has a piston which is operated by a force generated by the medical practitioners hand, rather than requiring use of a high pressure discharge providing dispensing gun, much like a caulking gun, as is necessary with prior art compositions. It is desirable that the particles exhibit an injection force of no more than about 20 pounds, more preferably no more than about 15 pounds and still more preferably no more than about 10 pounds as measured by the injection force described in detail in Example 1, below. Injection force provides a practical and easily carried out test of injectability which it is believed is more meaningful than measuring the viscosity of a plurality of flowable particles generally having only interstitial carrier liquid.

As the composition 17 is injected into the tissues 7 adjacent the wall 5 of the enlarged lumen 3, the diameter of the enlarged lumen 3 is observed through the cystoscope 9 for constriction. The composition 17 constricts the wall 5, decreasing the diameter of the once enlarged lumen 3 into a constricted area 23. With increasing volume of the composition 17, the constricted area 23 is further decreased. Once the desired degree of constriction is attained at the constricted area 23, injection of the composition 17 is stopped and the hypodermic needle 15 (or 31) is removed from the site of insertion. The constricted area 23, as observed through the cystoscope 9, would generally have an equal or smaller diameter than the diameter 25 of the rest of the urethra 1. When injections are made about the ureter and when injections are made in males the needle 15 is passed through the working channel 12 of the cystoscope 9 and through the wall of the urethra/ureter rather than through adjacent tissue as illustrated in FIG. 3.

Referring to FIG. 2, there is shown a solid structure 27 comprising swollen hydrogel particles 19. When no carrier or only a very small amount, for example only the interstitial volume of carrier is used, the initial volume of the physiologically acceptable composition 17 is maintained. With the initial volume maintained, the constricted area 23 retains the desired degree of constriction. In addition, since the swollen hydrogel 19 is able to remain in place due to its particle size and insolubility in body fluids, the degree of constriction is substantially permanent. The literature is unclear in this area but it appears to indicate that particles of 25 microns, 50 microns or 80 microns in size will resist migration and the particles of the invention can be and are preferably of at least the minimum size stated.

Generally, the hydrogel will be swelled by being positioned when not yet swollen or when only partially swollen, in an aqueous solution containing an appropriate quantity of the organic compound. However, it is possible to first swell the hydrogel, partially or completely, with water and then to immerse it in the organic compound or in an aqueous solution of the organic compound so that the organic compound may enter into the already, partially or completely, water swollen hydrogel. For ease of operation and for best results, the first method mentioned is preferred.

In certain situations it can be desirable to add a radiopaque material to the hydrogel particles, preferably barium sulfate, bismuth subcarbonate, tantalum, tungsten, silver or mixtures thereof. The radiopaque material can be incorporated into the unswollen hydrogel from which the swollen hydrogel particles are formed, by melt mixing or, in the case of gels by dispersing into the solutions prior to crosslinking them to form gels. By having the swollen hydrogel particles radiopaque, the constricted site 23, normally radiolucent to X-rays as with many other body tissues, will no longer be radiolucent. Consequently, the constricted area 23 can be examined by X-ray imaging or fluoroscopy which may help to visualize the internal shape within the tissue since this cannot be seen by direct observation through the cystoscope 9.

The invention will be better understood by reference to the following experimental examples:

EXAMPLE 1

Injection Force Tests:

As all bulking agent formulations (the term bulking agent refers to the injectate) are designed for endoscopic injection, a standardized test was designed to test the ultimate force required to move the bulking agent through specific needles. Use of this test permitted objective decision-making in process and formulation changes and the evaluation of delivery systems. A Lloyd, or Instron with a series of load cells rated between 5 and 500 N was the equipment used.

The load cell was rezeroed between tests. The deformation of the rubber seal within the syringe plunger prevents complete unloading of the system via extrusion of bulking agent, and a residual load remains against the sensor. Backing off the crossarm and resetting the system results in a more accurate reading of the injection force.

When testing the bulking agent, the force curve generated by the instrument was observed. The test was continued long enough for the force reading to stabilize, and the curve to reach the asymptotic ultimate force. The general setting for the extension limit of the cross-arm was 0.5 inches, given the example below.

The purpose was to provide objective data on force required in injecting bulking formulas through syringe system. The material used was a bulking agent specimen. The equipment used was a Lloyd Material Testing System, 3 cc plastic syringe, 19 gauge needle, syringe fixtures, collection vial, and safety glasses. The Lloyd apparatus was a Chatillon Instron compression/tensile tester.

The injection forces of the swollen hydrogel particles (PEO particles 45–125 microns hydrated in PEG 400 (molecular weight nominally 400) solutions) with a range of PEG concentrations from 0% to 50%, remainder water, were measured using the specified procedure. The hydrogel particles, without a carrier liquid but still wet by the swelling solution, were filled into 3 cc syringes. The syringes were connected to 4" long 19 gauge needles. The syringe with needle was placed into a fixture where the force required to inject the material could be measured in a compression mode. The rate of injecting the suspensions were measured between 1 in/min to 5.5 in/min. This test defines IF as the force, in pounds, exhibited by the swollen particles.

| Constant Volume Injection Force (IF) Swollen Particles @ 5.5 in/min | |
|---|---|
| 0% PEG | 27.83 lb |
| 0.5% PEG | 28.55 lb |
| 1% PEG | 27.77 lb |
| 1.5% PEG | 29.30 lb |
| 2% PEG | 9.90 lb |
| 2.5% PEG | 8.81 lb |
| 3% PEG | 7.32 lb |
| 3.5% PEG | 5.37 lb |
| 4% PEG | 5.36 lb |
| 6% PEG | 9.19 lb |
| 8% PEG | 13.37 lb |
| 10% PEG | 12.26 lb |
| 25% PEG | 18.98 lb |
| 50% PEG | 29.38 lb |

As can be seen from the above table, it was unexpectedly discovered that at both low (up to 1.5% or so) and high (over about 25% or so) concentrations of PEG in the swelling solution, relatively high injection forces were needed to inject the swollen particles. Between these limiting values the injection force required was far less, i.e., required application of a significantly lower IF than when no organic compound was present, and hand operated syringes were fully adequate to inject the compositions. As will be appreciated, the reduction in IF can be varied depending on the concentration and type of water soluble organic compound utilized. Nevertheless, it is generally preferred that the concentration of the organic compound be adjusted so as to reduce the IF to no more than about 85%, 80%, or 70% of its value when no organic compound is present, more preferably to no more than about 50% of such value and still more preferably to no more than about 35%, 30%, or 20% of such value.

Teflon particles in glycerin and silicone particles in a PVP solution injection forces were both measured to be above 40 lb and caused the syringe to fail.

The syringe force testing showed that the forces for the swollen hydrogel particles were significantly lower than those for slurries of Teflon particles in glycerin or silicone particles in PVP solution. From this data it follows that, for use without an assist device, and with the particular syringe used, the IF should be limited to less than about 40 lb and it is preferred that the injection force be limited to less than or equal to about 20 lb so as to allow use of a conventional non-assist type syringe. More preferably, the injection force can be limited to less than or equal to about 14 lb.

INDUSTRIAL APPLICABILITY

Although the physiologically acceptable composition is typically inserted into tissues adjacent to a tissue structure to deform the selected tissue structure, a specific use for the composition is for increasing urine flow resistance in patients having urinary incontinence. The physiologically acceptable composition is inserted into the tissues surrounding the patient's urethra adjacent to the patient's urethral sphincter. The presence of the physiologically acceptable composition allows constriction of the urethra thereby decreasing urine flow from the bladder. As a result the incontinent patient will have an improved control of urine flow.

The physiologically acceptable composition can also be used in patients having vesicoureteral reflux. Similar to the method used in increasing urine flow resistance in patients having urinary incontinence, the physiologically acceptable composition is injected into the tissues adjacent to the patient's ureteral orifice thereby constricting the ureteral duct. With the constriction, the undesirable backflow of urine from the bladder up the ureter is prevented.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

The invention claimed is:

1. A physiologically acceptable composition comprising a plurality of physiologically acceptable hydrogel particles formed from hydrophilic crosslinked particles of polymers selected from the group consisting of polyethylene oxide polymer or copolymer, a polyvinylpyrrolidone polymer or copolymer, a polyvinyl alcohol polymer or copolymer, a pHema polymer or copolymer, a Hypan polymer or copolymer, a starch glycolate polymer or copolymer salt, and a polyacrylic acid polymer or copolymer which have been swollen by an aqueous medium that contains a water soluble organic compound having a molecular weight of from about 200 up to about 50,000 and that is selected from the group consisting of polyethylene glycol, polyvinylprrolidone polymer, polyvinylprrolidone copolymer, dextran polymer, dextran copolymer, polyoxyalkylene ether, polyacrylic acid, polyvinyl pyridine, polylysine, polyarginine, poly aspartic acid and poly glutamic acid, the concentration of the organic compound being such that the resulting particles require application of an injection force of at least 30% less than that required for the same composition when no organic compound is present, the swollen hydrogel particles is insoluble in body fluids.

2. A physiologically acceptable composition as set forth in claim 1 wherein the swollen hydrogel particles have a particle size sufficient to resist migration from a site of insertion into a patient's body.

3. A physiologically acceptable composition as set forth in claim 2 wherein the hydrogel particles have been swollen from about 25 to about 2,000 percent by the solution.

4. A physiologically acceptable composition as set forth in claim 1 wherein the swollen hydrogel particles further comprise a radiopaque material.

5. A physiologically acceptable composition as set forth in claim 2 wherein the particle size following hydration is at least about 50 microns.

6. A physiologically acceptable composition as set forth in claim 5 wherein the swollen hydrogel particles further comprise a radiopaque material.

7. A physiologically acceptable composition as set forth in claim 1 which requires an injection force of no more than about 70% of that needed when no organic compound is present.

8. A physiologically acceptable composition as set forth in claim 1 which requires an injection force of no more than about 50% of that needed when no organic compound is present.

9. A physiologically acceptable composition as set forth in claim 1 which requires an injection force of no more than about 35% of that needed when no organic compound is present.

10. A physiologically acceptable composition as set forth in claim 1 wherein the swollen particles have a particle size of at least about 80 microns.

11. A physiologically acceptable composition as set forth in claim 1, wherein the hydrogel particles are a polyethylene oxide polymer or copolymer and the organic compound is polyethylene glycol.

* * * * *